(12) United States Patent
Kuwada et al.

(10) Patent No.: US 10,606,545 B2
(45) Date of Patent: Mar. 31, 2020

(54) DISPLAY APPARATUS, SCANNER, AND NON-TRANSITORY COMPUTER READABLE MEDIUM

(71) Applicant: FUJI XEROX CO., LTD., Tokyo (JP)

(72) Inventors: Yoshitaka Kuwada, Kanagawa (JP); Jungo Harigai, Kanagawa (JP); Hirokazu Ichikawa, Kanagawa (JP); Ryosuke Higashikata, Kanagawa (JP)

(73) Assignee: FUJI XEROX CO., LTD., Tokyo (JP)

( * ) Notice: Subject to any disclaimer, the term of this patent is extended or adjusted under 35 U.S.C. 154(b) by 0 days.

(21) Appl. No.: 15/984,440

(22) Filed: May 21, 2018

(65) Prior Publication Data

US 2019/0129674 A1 May 2, 2019

(30) Foreign Application Priority Data

Oct. 30, 2017 (JP) ................... 2017-209558

(51) Int. Cl.
| | | |
|---|---|---|
| *G06F 3/147* | (2006.01) | |
| *G01N 21/55* | (2014.01) | |
| *G06T 7/40* | (2017.01) | |
| *G06T 15/04* | (2011.01) | |
| *G01N 21/00* | (2006.01) | |

(Continued)

(52) U.S. Cl.
CPC ............ *G06F 3/147* (2013.01); *G01N 21/00* (2013.01); *G01N 21/55* (2013.01); *G06T 7/40* (2013.01); *G06T 15/04* (2013.01); *G09G 3/00* (2013.01); *G01N 21/57* (2013.01); *G01N 2021/556* (2013.01); *G06T 17/00* (2013.01);

(Continued)

(58) Field of Classification Search
None
See application file for complete search history.

(56) References Cited

U.S. PATENT DOCUMENTS

| | | | | |
|---|---|---|---|---|
| 8,035,607 | B2 * | 10/2011 | Otome ................. | G09G 3/3648 345/102 |
| 2003/0090555 | A1 * | 5/2003 | Tatsumi ................. | B41J 2/2114 347/101 |

(Continued)

FOREIGN PATENT DOCUMENTS

| | | |
|---|---|---|
| JP | 2003-281565 | 10/2003 |
| JP | 2005-115645 | 4/2005 |

(Continued)

*Primary Examiner* — Yanna Wu

(74) *Attorney, Agent, or Firm* — JCIPRNET

(57) ABSTRACT

A display apparatus includes a diffuse reflection image acquiring unit, a specular reflection image acquiring unit, a difference image acquiring unit, a reflectance distribution function calculating unit, and a display. The diffuse reflection image acquiring unit acquires a diffuse reflection image of an object surface. The specular reflection image acquiring unit acquires a specular reflection image of the object surface. The difference image acquiring unit acquires a difference image between the diffuse reflection image and the specular reflection image. The reflectance distribution function calculating unit calculates a reflectance distribution function of the object surface by using the diffuse reflection image and the difference image. The display displays a reflection color of the object surface in accordance with a change of orientation of the object surface by using the reflectance distribution function.

6 Claims, 13 Drawing Sheets

(51) Int. Cl.
  *G09G 3/00*      (2006.01)
  *G06T 17/00*     (2006.01)
  *G01N 21/57*     (2006.01)
(52) U.S. Cl.
  CPC ............... *G06T 2207/10008* (2013.01); *G06T 2207/10152* (2013.01); *G06T 2207/20224* (2013.01)

(56) References Cited

U.S. PATENT DOCUMENTS

2005/0073939 A1   4/2005   Sakaguchi et al.
2016/0116558 A1*  4/2016   Grodzki ............. G01R 33/4833
                                                   324/309
2016/0371880 A1   12/2016  Ide

FOREIGN PATENT DOCUMENTS

JP    2011-061731    3/2011
JP    2015-49691     3/2015

* cited by examiner

DIFFUSE REFLECTION IMAGE
SPECULAR REFLECTION IMAGE

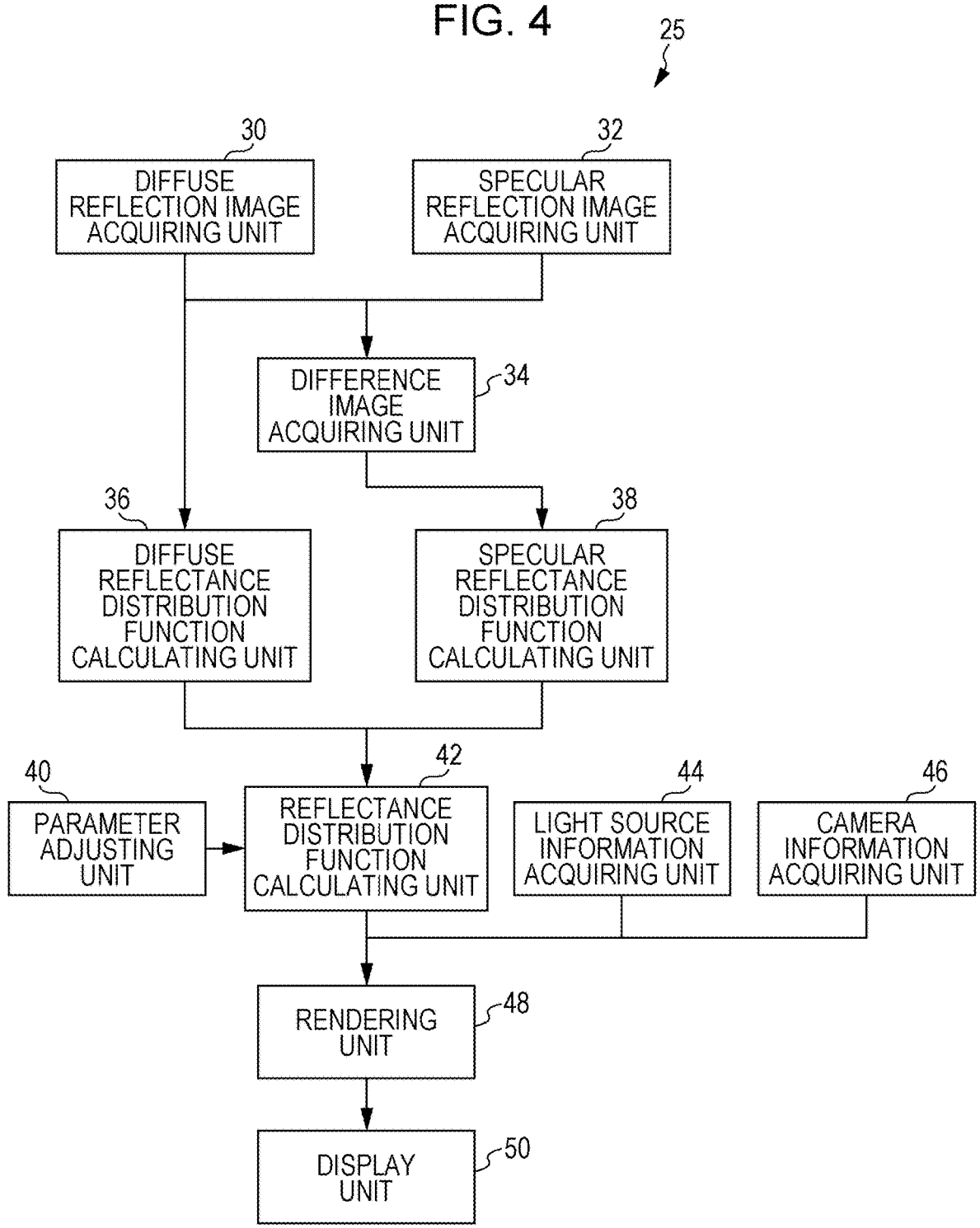

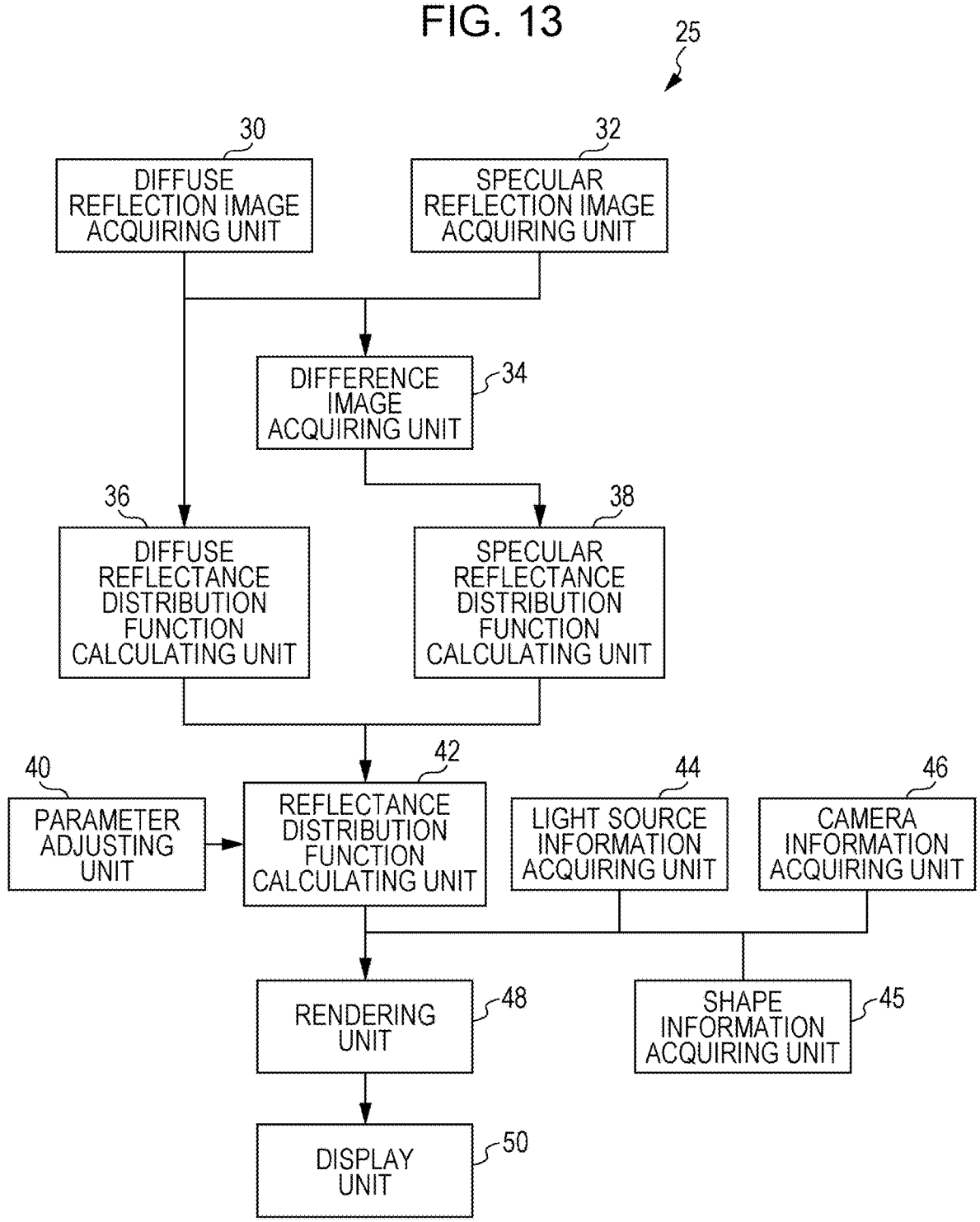

DIFFUSE REFLECTION IMAGE
SPECULAR REFLECTION IMAGE
DIFFERENCE IMAGE

DISPLAY APPARATUS, SCANNER, AND NON-TRANSITORY COMPUTER READABLE MEDIUM

CROSS-REFERENCE TO RELATED APPLICATIONS

This application is based on and claims priority under 35 USC 119 from Japanese Patent Application No. 2017-209558 filed Oct. 30, 2017.

BACKGROUND

Technical Field

The present invention relates to display apparatuses, scanners, and non-transitory computer readable media.

SUMMARY

According to an aspect of the invention, there is provided a display apparatus including a diffuse reflection image acquiring unit, a specular reflection image acquiring unit, a difference image acquiring unit, a reflectance distribution function calculating unit, and a display. The diffuse reflection image acquiring unit acquires a diffuse reflection image of an object surface. The specular reflection image acquiring unit acquires a specular reflection image of the object surface. The difference image acquiring unit acquires a difference image between the diffuse reflection image and the specular reflection image. The reflectance distribution function calculating unit calculates a reflectance distribution function of the object surface by using the diffuse reflection image and the difference image. The display displays a reflection color of the object surface in accordance with a change of orientation of the object surface by using the reflectance distribution function.

BRIEF DESCRIPTION OF THE DRAWINGS

Exemplary embodiments of the present invention will be described in detail based on the following figures, wherein:

FIG. 4 illustrates the configuration of a display apparatus according to an exemplary embodiment;

FIG. 13 illustrates the configuration of a display apparatus according to another exemplary embodiment;

DETAILED DESCRIPTION

Exemplary embodiments of the present invention will be described in detail below with reference to the drawings.

First Exemplary Embodiment

1. Configuration of Scanner (Texture Scanner)

Figure 1:
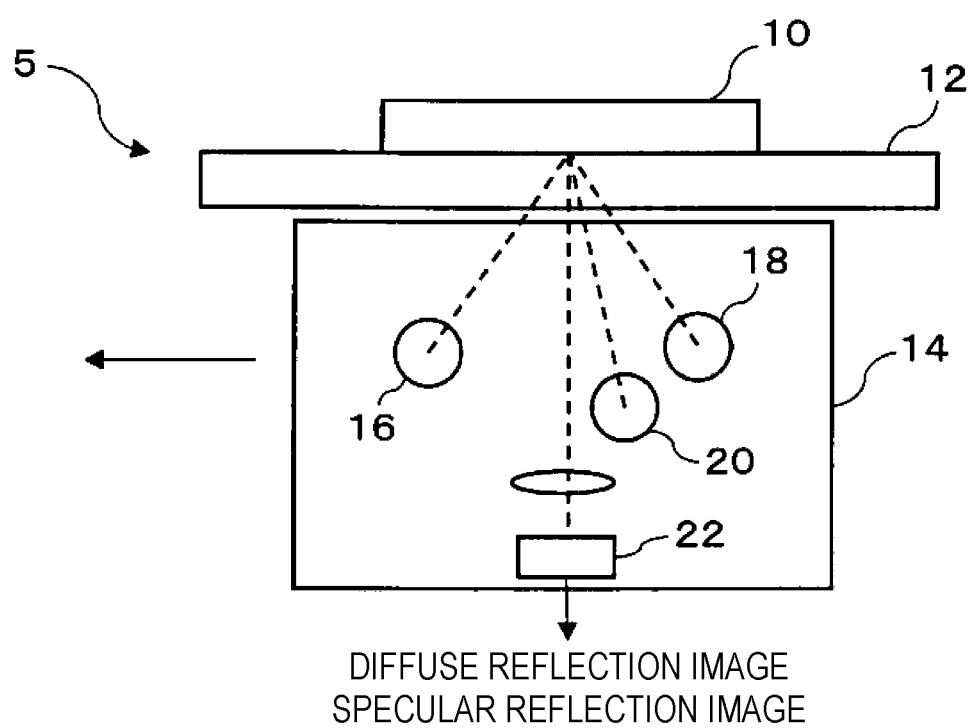
FIG. 1 illustrates the configuration of a texture scanner according to an exemplary embodiment.

FIG. 1 illustrates the configuration of a scanner (texture scanner) 5 according to a first exemplary embodiment for acquiring an image of a surface of a planar object 10.

The texture scanner 5 optically reads the surface characteristics of the planar object 10 and generates an image signal expressing the read result. The image signal generated by the texture scanner 5 includes an image signal based on diffuse reflection light and an image signal based on specular reflection light. The texture scanner 5 includes a platen glass member 12, a carriage 14, light sources 16, 18, and 20, and a sensor 22.

In the texture scanner 5, each of the components shown in FIG. 1 has a width set in the direction orthogonal to the plane of the drawing. This direction is a first scanning direction of the texture scanner 5. A direction indicated by an arrow in FIG. 1 is a second scanning direction of the texture scanner 5.

The platen glass member 12 is a transparent glass plate that supports the planar object 10 to be read. The platen glass member 12 may alternatively be, for example, an acrylic plate instead of a glass plate. Although not shown, a platen cover that covers the platen glass member 12 to block off external light may be provided such that the planar object 10 is interposed between the platen cover and the platen glass member 12.

When the planar object 10 is to be read, the carriage 14 moves at a predetermined speed in the second scanning direction. The carriage 14 contains the light sources 16, 18, and 20 therein. The light source 16 is a front light source that radiates light at an incident angle of 45°, which is a first incident angle, relative to the normal direction of the planar object 10 so as to radiate light for reading diffuse reflection light from the planar object 10. The light source 18 is a rear light source that radiates light at an incident angle of 45° relative to the normal direction of the planar object 10 so as to radiate light for reading diffuse reflection light from the planar object 10. The light source 20 is a rear light source that radiates light at an incident angle of 10°, which is a second incident angle, relative to the normal direction of the planar object 10 so as to radiate light for reading specular reflection light from the planar object 10.

The light source 20 is provided at a position where it does not block a principal ray of the reflection light. Although the incident angle of the light radiated by the light source 20 is 10° in this exemplary embodiment, the incident angle may be about 5° to 10°. With regard to the reflection light of the light radiated by the light source 20, a ray of the light traveling in the normal direction of the planar object 10 is read.

It is desirable that the light source 20 radiate light at a small angle. If the angle of the light radiated by the light source 20 is relatively large, for example, a cover that limits the angle of the light radiated by the light source 20 may be provided. Moreover, since the light source 20 is provided for reading luster information of the planar object 10, it is desirable that the luminance be uniform and continuous as much as possible in the first scanning direction, as compared with the light sources 16 and 18.

Examples that may satisfy the conditions of the light source 20 include a fluorescent lamp and a rare gas fluorescent lamp (such as a xenon fluorescent lamp). The light source 20 may have multiple white light emitting diodes (LEDs) arranged in the first scanning direction, and the luminance distribution in the first scanning direction may be made uniform by using, for example, a diffuser.

The carriage 14 also contains therein an imaging optical system and the sensor 22. The imaging optical system is constituted of a reflecting mirror and an imaging lens and causes the sensor 22 to form images of diffuse reflection light and specular reflection light components from the planar object 10. The sensor 22 receives the diffuse reflection light and specular reflection light components imaged by the imaging optical system so as to generate an image signal according to the received light. The sensor 22 is constituted of a light receiving element, such as a charge-coupled-device (CCD) linear image sensor or a complementary metal-oxide semiconductor (CMOS) image sensor, and converts the received light into a signal expressing the magnitude of the received light. Moreover, the sensor 22 includes a color filter and generates an image signal expressing the color of the planar object 10. The sensor 22 outputs, to an external apparatus, a diffuse reflection image signal obtained by receiving the diffuse reflection light and a specular reflection image signal obtained by receiving the specular reflection signal.

In a normal scanner (or an image reader), the light source 16 (or the light source 18) radiates light at an incident angle of 45° relative to the normal direction of the planar object 10 so as to read a diffuse reflection light from the planar object 10. In contrast, the texture scanner 5 according to this exemplary embodiment additionally causes the light source 20 to radiate light at an incident angle of 10° relative to the normal direction of the planar object 10 so as to read specular reflection light from the planar object 10.

Figure 2A:
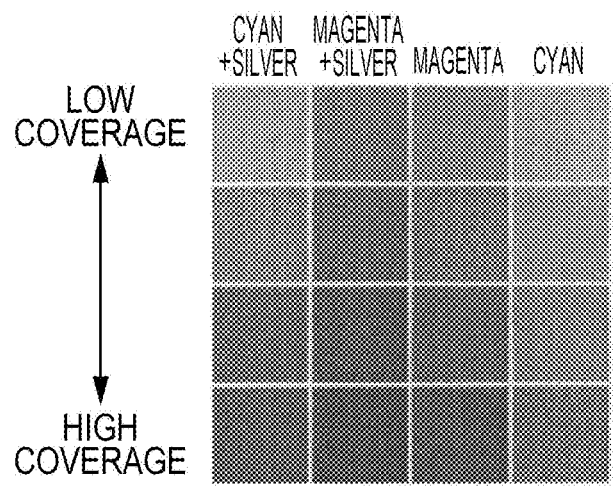
FIGS. 2A to 2C illustrate a diffuse reflection image, a specular reflection image, and a difference image therebetween acquired by the texture scanner.
Figure 2B:
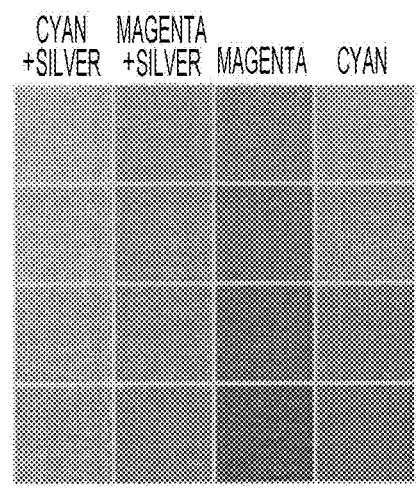

FIGS. 2A and 2B illustrate examples of a diffuse reflection image and a specular reflection image of the planar object 10 obtained by the texture scanner 5 shown in FIG. 1. The planar object 10 is a printed material output based on electrophotography by varying the coverage, which is a toner amount during printing, using a cyan+silver toner, a magenta+silver toner, a magenta toner, and a cyan toner. FIG. 2A illustrates a diffuse reflection image obtainable by a normal scanner. FIG. 2B is a specular reflection image in which a metallic luster section of the planar object 10 is particularly glossy. In this exemplary embodiment, a metallic luster region of the planar object 10 is extracted by using these two images. Specifically, a difference image is acquired by calculating a difference between the diffuse reflection image and the specular reflection image.

Figure 2C:
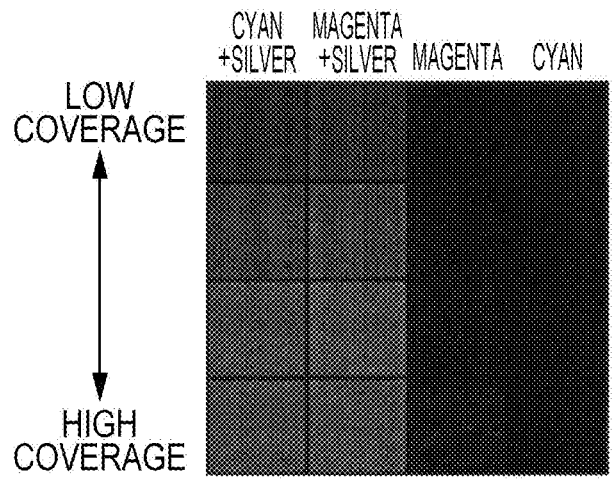

FIG. 2C illustrates a difference image between the diffuse reflection image shown in FIG. 2A and the specular reflection image shown in FIG. 2B. In the image, the metallic luster region (i.e., the region including the silver toner in actuality) is clearly shown, and the difference in reflectance of the metallic luster is also shown.

In the texture scanner 5 shown in FIG. 1, a value obtained by dividing an incident angle by an acceptance angle is fixed at each pixel of a two-dimensional plane so that, by calculating a difference between an image acquired under a diffuse reflection condition (i.e., incident angle of 45°) and an image acquired under a specular reflection condition (i.e., incident angle of 10°), metallic luster information is properly extracted. Specifically, by performing a simple difference calculation, the metallic luster region and the reflectance (i.e., specular reflectance of the two-dimensional plane) may be acquired at one time. With regard to the diffuse reflection condition (i.e., incident angle of 45°) and the specular reflection condition (i.e., incident angle of 10°), calibration is performed using the same white calibration plate. Therefore, luster information may be extracted by performing a simple difference calculation.

Figure 3A:
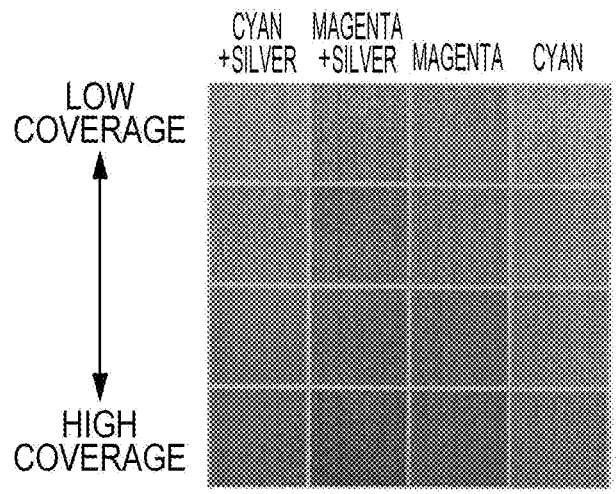
FIGS. 3A to 3C illustrate a diffuse reflection image, a specular reflection image, and a difference image therebetween acquired by a camera.
Figure 3B:
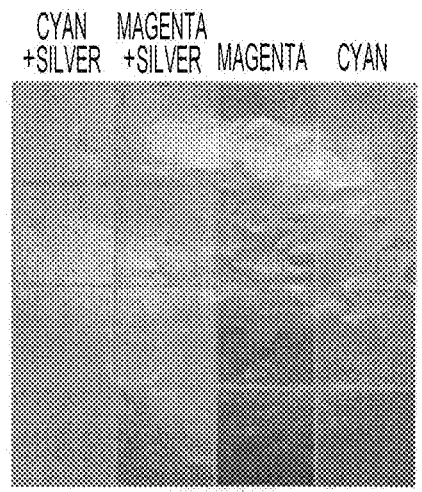
Figure 3C:
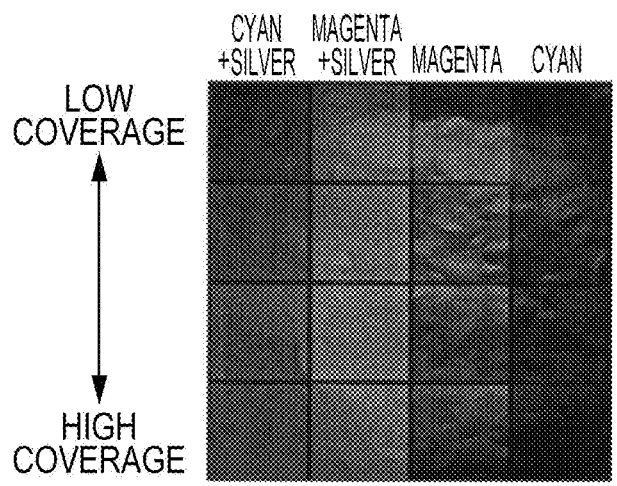

FIGS. 3A to 3C illustrate images of the same planar object 10 acquired using a camera for a comparison and show an image acquired under the diffuse reflection condition (i.e., incident angle of 45°) and an image acquired under the specular reflection condition (i.e., incident angle of 10°) by using a white LED. In the case of a camera, the incident angle/acceptance angle condition varies at each pixel of the two-dimensional plane so that the image acquired under the specular reflection condition has uneven luster. Thus, even if a difference between the image acquired under the diffuse reflection condition and the image acquired under the specular reflection condition is acquired, it is difficult to properly extract metallic luster information (i.e., silver toner region and reflectance) of the two-dimensional plane. Therefore, in order to properly extract metallic luster information by using a camera, it is necessary to acquire images from a larger number of angles and estimate the metallic luster information from the acquired image data, which implies that a large amount of calculation is necessary. Thus, in order to properly acquire luster information of the surface of an object having a large surface area (e.g., a printed material of an A3 sheet size), a large amount of calculation is necessary.

2. Configuration of Display Apparatus

FIG. 4 illustrates the overall configuration according to this exemplary embodiment. A display apparatus 25 is configured to display the texture of the planar object 10 by acquiring and processing the diffuse reflection image and the specular reflection image obtained by the texture scanner 5 shown in FIG. 1.

The display apparatus 25 includes a diffuse reflection image acquiring unit 30, a specular reflection image acquiring unit 32, a difference image acquiring unit 34, a diffuse reflectance distribution function calculating unit 36, a specular reflection distribution function calculating unit 38, a parameter adjusting unit 40, a reflectance distribution function calculating unit 42, a light source information acquiring unit 44, a camera information acquiring unit 46, a rendering unit 48, and a display unit 50.

The diffuse reflection image acquiring unit 30 and the specular reflection image acquiring unit 32 respectively acquires the diffuse reflection image and the specular reflection image obtained by the texture scanner 5. The diffuse reflection image acquiring unit 30 and the specular reflection image acquiring unit 32 may both be connected to the texture scanner 5 and acquire these images from the texture scanner 5, or may acquire these images from a server connected to the texture scanner 5 via a network.

The difference image acquiring unit 34 acquires a difference image by calculating a difference between the diffuse reflection image and the specular reflection image. There are two kinds of difference images, namely, a difference image obtained by subtracting the diffuse reflection image from the specular reflection image (specular reflection image-diffuse reflection image) and a difference image obtained by subtracting the specular reflection image from the diffuse reflection image (diffuse reflection image-specular reflection image), and the difference image acquiring unit 34 calculates at least one of these difference images.

The diffuse reflectance distribution function calculating unit 36 calculates a diffuse reflectance distribution function of the planar object 10 by using the diffuse reflection image. For example, in accordance with the Lambert reflection model, the diffuse reflectance distribution function calculating unit 36 uses a diffuse reflectance distribution function $\rho_d \cdot \cos \theta_i$, where $\rho_d$ denotes diffuse reflectance with respect to incident light and $\theta_i$ denotes the incident angle, so as to calculate the diffuse reflectance $\rho_d$ as a parameter from the diffuse reflection image.

The specular reflection distribution function calculating unit 38 calculates a specular reflectance distribution function of the planar object 10 by using the difference image. For example, in accordance with the Phong reflection model, the specular reflection distribution function calculating unit 38 uses a specular reflectance distribution function $\rho_s \cdot \cos^n \gamma$, where $\rho_s$ denotes specular reflectance, $\gamma$ denotes an angle formed between a specular reflection direction and a visual line direction, and n denotes a specular reflection index, so as to calculate the specular reflectance $\rho_s$ and the specular reflection index n as parameters from the difference image. In a case where two difference images are acquired by the difference image acquiring unit 34 and the specular reflectance distribution function is to be calculated by using these two difference images, the specular reflection distribution function calculating unit 38 uses a specular reflectance distribution function $\rho_{s1} \cdot \cos^{n1} \gamma$ for the difference image (specular reflection image-diffuse reflection image) and a specular reflectance distribution function $\rho_{s2} \cdot \cos^{n2} \gamma$ for the difference image (diffuse reflection image-specular reflection image) so as to calculate $\rho_{s1}$, $\rho_{s2}$, n1, and n2 as parameters from these difference images.

The reflectance distribution function calculating unit 42 uses the diffuse reflectance distribution function calculated by the diffuse reflectance distribution function calculating unit 36 and the specular reflectance distribution function calculated by the specular reflection distribution function calculating unit 38 so as to calculate a reflectance distribution function for each pixel of the planar object 10. For example, in accordance with the Lambert reflection model and the Phong reflection model, the reflectance distribution function calculating unit 42 calculates the reflectance distribution function as follows:

Reflectance Distribution Function=Diffuse Reflectance Distribution Function+Specular Reflectance Distribution Function Based on the reflectance distribution function calculated by the reflectance distribution function calculating unit 42, various parameters set by the parameter adjusting unit 40, light source information (i.e., light source direction) acquired by the light source information acquiring unit 44, and camera information (i.e., visual line direction) acquired by the camera information acquiring unit 46, the rendering unit 48 renders a three-dimensional model on a virtual screen set within a virtual three-dimensional space so as to computer-graphically reproduce the texture of the planar object 10, and causes the display unit 50 to display the three-dimensional model. The rendering process is widely known. For example, the rendering process may be performed by using the radiosity technique or the ray tracing technique in view of interreflection.

The display apparatus 25 shown in FIG. 4 is specifically realized by a computer equipped with one or more processors, a memory, an input-output interface, a communication interface, and a display unit. The processor reads a processing program stored in a nonvolatile memory, such as a read-only memory (ROM), a hard disk drive (HDD), or a solid state drive (SSD), and executes the processing program so as to realize the function of each component. For example, the memory functions as the diffuse reflection image acquiring unit 30 and the specular reflection image acquiring unit 32 so as to store a diffuse reflection image and a specular reflection image, and the processor executes the processing program so as to function as the difference image acquiring unit 34, the diffuse reflectance distribution function calculating unit 36, the specular reflection distribution function calculating unit 38, the reflectance distribution function calculating unit 42, and the rendering unit 48. Specifically, the processor reads the diffuse reflection image and the specular reflection image stored in the memory to calculate a difference therebetween and stores a generated difference image in the memory. Then, the processor reads the diffuse reflection image stored in the memory to calculate a diffuse reflectance distribution function, stores the parameters thereof in the memory, reads the difference image stored in the memory to calculate a specular reflectance distribution function, and stores the parameters thereof in the memory. The processor calculates, for example, a reflectance distribution function as a sum of the diffuse reflectance distribution function and the specular reflectance distribution function. The steps executed in the processor are as follows.

Step a: Acquire a diffuse reflection image of the planar object 10 and store the image in the memory.

Step b: Acquire a specular reflection image of the planar object 10 and store the image in the memory.

Step c: Acquire a difference image between the diffuse reflection image and the specular reflection image and store the image in the memory. In this case, the difference image is acquired from the texture scanner 5 if the difference image is generated in and output from the texture scanner 5. If the difference image is not output from the texture scanner 5, a difference image is generated and acquired by calculating a difference between the diffuse reflection image and the specular reflection image.

Step d: Calculate a reflectance distribution function of the planar object 10 by using the diffuse reflection image and the difference image.

Step e: Cause the display unit 50 to display a change in reflection color of the planar object 10 caused by a difference in incident angle of light or viewing angle using the reflectance distribution function.

Step d further includes the following two steps.

Step d1: Calculate a diffuse reflectance distribution function by using the diffuse reflection image.

Step d2: Calculate a specular reflectance distribution function by using the difference image.

The one or more processors may each be constituted of a central processing unit (CPU) or a graphics processing unit (GPU). The display unit 50 is constituted of a liquid crystal display or an organic electroluminescence (EL) display. The parameter adjusting unit 40, the light source information acquiring unit 44, and the camera information acquiring unit 46 may each be constituted of an input device, such as a keyboard, a mouse, and/or a touchscreen.

A computer may be connected directly to the texture scanner 5 shown in FIG. 1, or may be connected to the texture scanner 5 and the server via a network. The computer includes a personal computer (PC), a tablet terminal, and a smartphone, and includes, for example, a tablet terminal equipped with a tilt sensor.

3. Reflectance Distribution Function

Next, the reflectance distribution function will be described.

Figure 5:
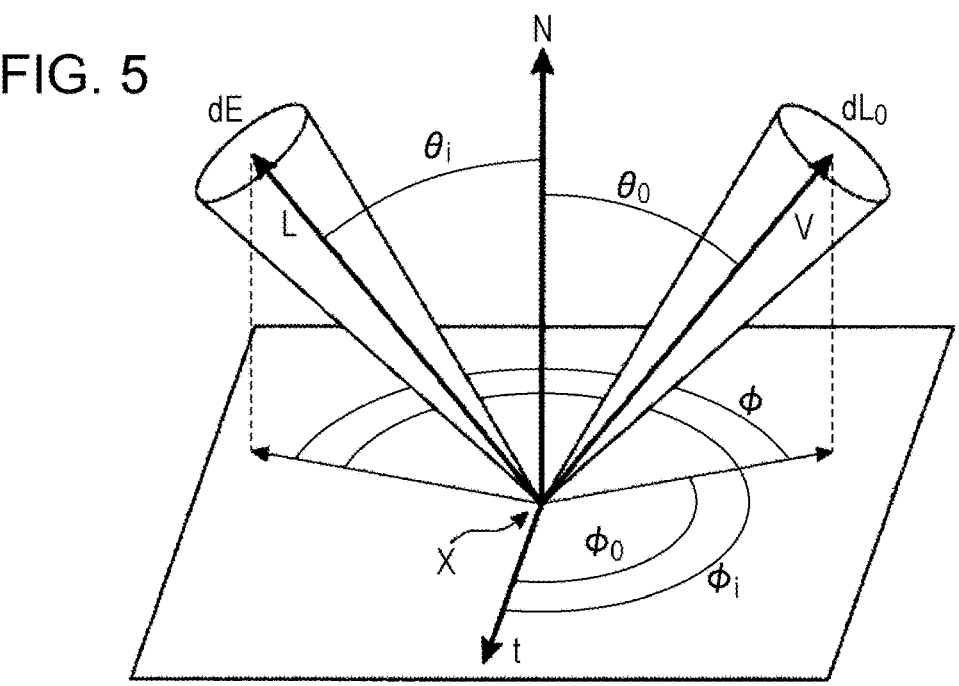
FIG. 5 illustrates geometric conditions for a bidirectional reflectance distribution function (BRDF)

FIG. 5 illustrates geometric conditions for a bidirectional reflectance distribution function (BRDF). A BRDF is a function expressing the ratio of a radiance $dL_O$ of light reflected at a micro solid angle of a visual line direction V to an irradiance dE of light entering from a micro solid angle of a light source direction L with respect to a certain point x on a reflection surface. Normally, a BRDF is measured using a measuring device capable of changing the incident angle or the acceptance angle, such as a goniophotometer. The measured value is referred to as "measured BRDF".

A BRDF is expressed with the following expression.

$$f(x, \theta_i, \phi_i, \theta_o, \phi_o) = \frac{dL_o(\theta_o, \phi_o)}{dE(\theta_i, \phi_i)}$$

Figure 6:
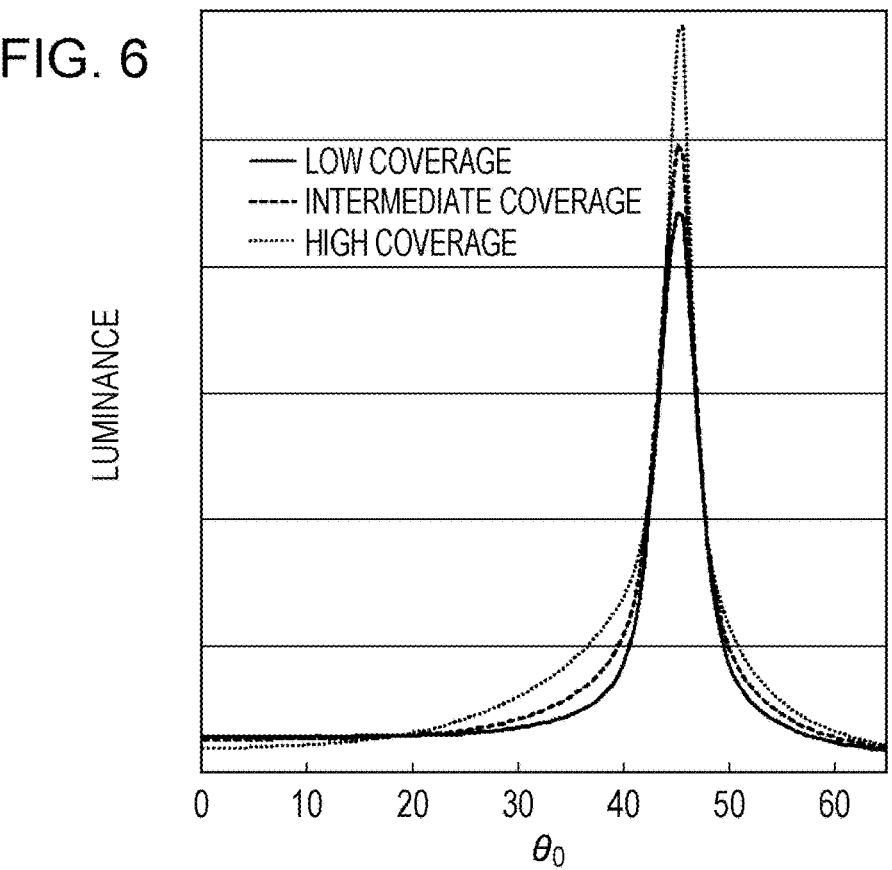
FIG. 6 is a graph illustrating an example of a measured BRDF.

FIG. 6 illustrates an example of a measured BRDF of a printed material output based on electrophotography by varying the coverage using a silver toner. A light-source-direction vector L and a visual-line-direction vector V are on the same plane (no $\phi$ component), an incident angle $\theta_i$ is 45°, and the horizontal axis denotes an acceptance angle $\theta_O$. A specular reflection angle is 45° when the incident angle is 45°.

According to FIG. 6, the luminance of specular reflection light increases with increasing coverage (i.e., metallic luster) of the silver toner.

Next, reflection models are generated by using the measured BRDF. The reflection models that may be used include the Lambert reflection model and the Phong reflection model.

Figure 7:
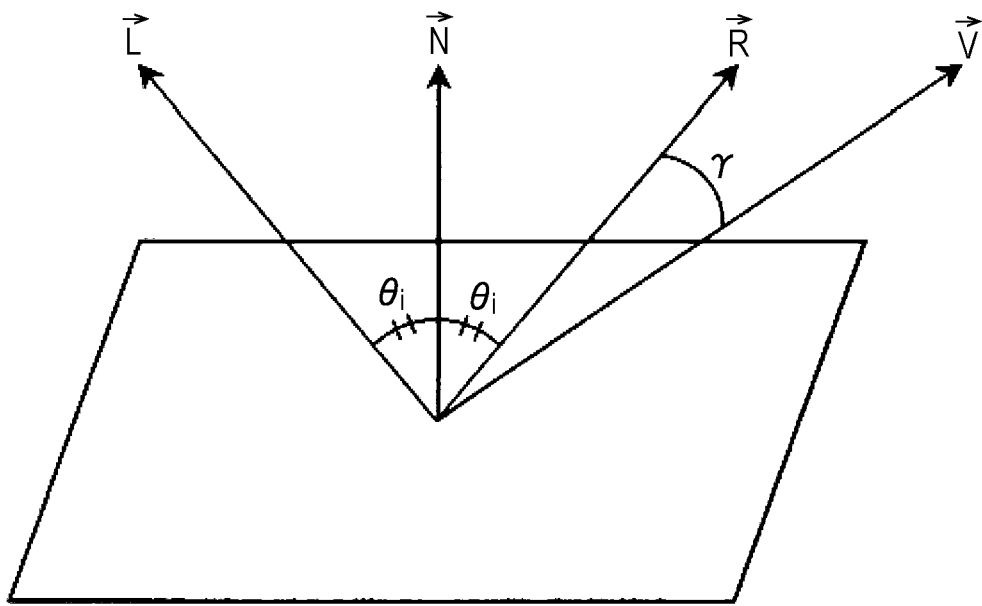
FIG. 7 illustrates the Phong reflection model.

FIG. 7 illustrates geometric conditions for the Lambert reflection model and the Phong reflection model.

Assuming that $I_i$ denotes the intensity of incident light, $\rho_d$ denotes diffuse reflectance, $\theta_i$ denotes an incident angle, $\rho_s$ denotes specular reflectance, n denotes a specular reflection index, and $\gamma$ denotes an angle formed between the specular reflection direction and the visual line direction, the intensity I of reflection light is expressed as follows:

$$I = I_i \cdot (\rho_d \cdot \cos \theta_i) + I_i \cdot (\rho_s \cdot \cos^n \gamma)$$

In this reflection model, parameters including the diffuse reflectance $\rho_d$, the specular reflectance $\rho_s$, and the specular reflection index n are estimated from the measured BRDF by performing a nonlinear regression analysis.

Figure 8:
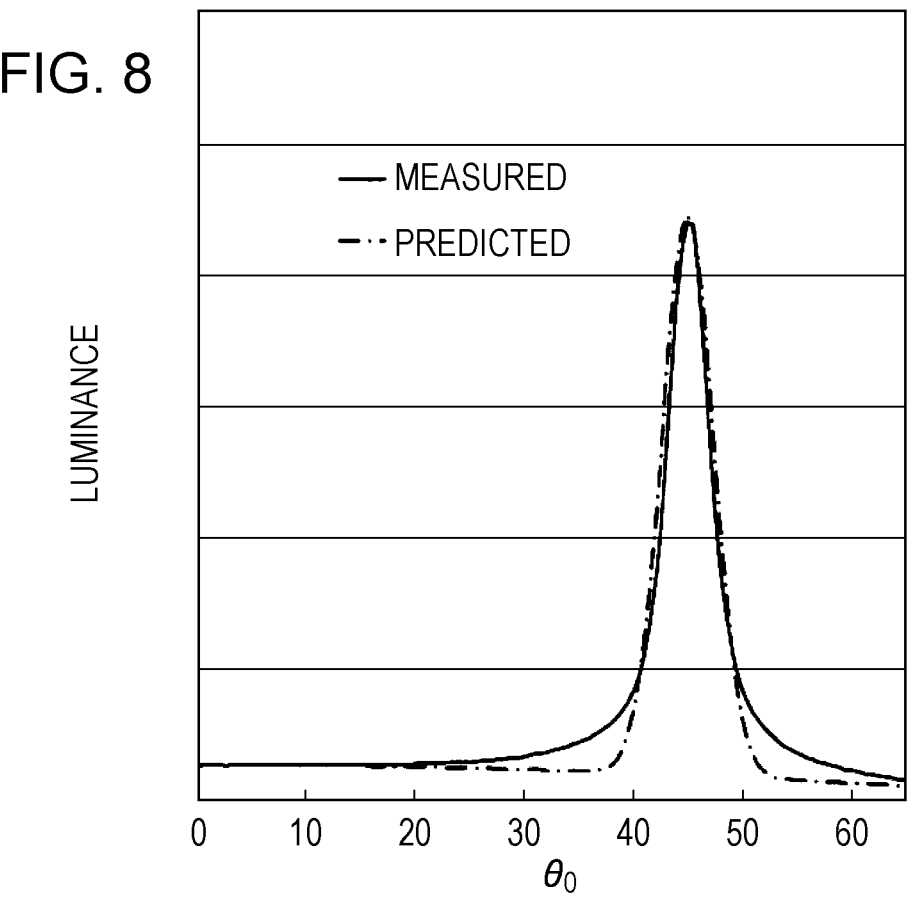
FIG. 8 is a graph illustrating an example where the measured BRDF is applied to the Phong reflection model.

FIG. 8 illustrates a predicted BRDF to which the measured BRDF with the low coverage shown in FIG. 6 is fitted in the example of the parameter estimation using the reflection model.

A BRDF acquiring method involves measuring the reflectance distribution by changing the incident angle and the acceptance angle, thus taking time for acquiring data. Moreover, it is necessary to optimize the coefficient of the reflection model by performing a nonlinear regression analysis on the acquired BRDF. Furthermore, if the sensor of the measuring device is not an area sensor (e.g., in a case of a photomultiplier), only an average BRDF within a measurement region is acquirable, thus making it difficult to acquire the BRDF of an object surface having an uneven BRDF for each region. Moreover, the difficulty in acquiring the BRDF of an object surface increases as the surface area of the object surface increases.

In contrast, in this exemplary embodiment, the diffuse reflectance distribution function is calculated from the diffuse reflection image, and the specular reflectance distribution function is calculated from the difference image. Since the difference image is properly extracted with respect to only the luster section of the planar object 10, a specular reflectance distribution function for each pixel of a two-dimensional plane may be calculated with high accuracy based on the difference image. Consequently, the texture of the object surface may be displayed by performing a simple calculation using a small amount of image data without having to acquire a BRDF.

Specifically, the reflectance distribution function calculating unit 42 uses the diffuse reflectance distribution function obtained by the diffuse reflectance distribution function calculating unit 36 and the specular reflection distribution function obtained by the specular reflection distribution function calculating unit 38 so as to calculate reflection light intensity I(x, y) in a two-dimensional plane by using the following expression in accordance with the Lambert reflection model and the Phong reflection model:

$$I(x,y) = I_i \cdot \{w_d \cdot G_d(x,y) \cdot \cos \theta_i\} + I_i \cdot \{w_s \cdot \{G_s(x,y) - G_d(x,y)\} \cdot \cos^n \gamma\}$$

where $\{w_d \cdot G_d(x, y) \cdot \cos \theta_i\}$ denotes a diffuse reflectance distribution function, $w_d$ denotes a diffuse reflection weighting factor, $G_d(x, y)$ denotes a diffuse reflection image, $\{w_s \cdot \{G_s(x, y) - G_d(x, y)\} \cdot \cos^n \gamma\}$ denotes a specular reflection distribution function, $w_s$ denotes a specular reflection weighting factor, $G_s(x, y)$ denotes a specular reflection image, and n denotes a specular reflection index. The difference image is a difference image (specular reflection image-diffuse reflection image), and a pixel with a negative difference value is set as 0. The reflection light intensity I(x, y) is calculated individually for each of R, G, and B components of the diffuse reflection image and the specular reflection image. As a result, a reflection color of the planar object 10 is calculated.

The diffuse reflectance distribution function calculating unit 36 calculates diffuse reflectance from the diffuse reflection image and the diffuse reflection weighting factor, and the specular reflectance distribution function calculating unit 38 calculates specular reflectance from the difference image and the specular reflection weighting factor. In this reflection model, the parameters including the diffuse reflection weighting factor $w_d$, the specular reflection weighting factor $w_s$, and the specular reflection index n are set in advance to fixed values by the parameter adjusting unit 40 in accordance with the reflection characteristics of the target object and the output characteristics of the display apparatus 25. If the target object is of the same material, as in the case of the silver toner in FIG. 6, a change of luster similar to that of an actual object may be reproduced even by setting the specular reflection index n to a fixed value.

In this embodiment, since the incident angle/acceptance angle condition is fixed by using the texture scanner 5 shown in FIG. 1, a large number of images is not necessary, unlike a case where a camera is used. Moreover, the reflectance distribution function is calculated for each pixel of a two-dimensional plane from the diffuse reflection image and the difference image, without having to estimate parameters by performing a nonlinear regression analysis on an acquired BRDF.

Figure 9A:
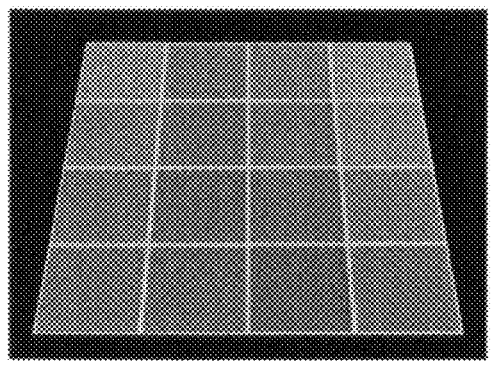
FIGS. 9A and 9B illustrate images (computer graphics (CG) images) displayed on a display unit according to an exemplary embodiment.
Figure 9B:
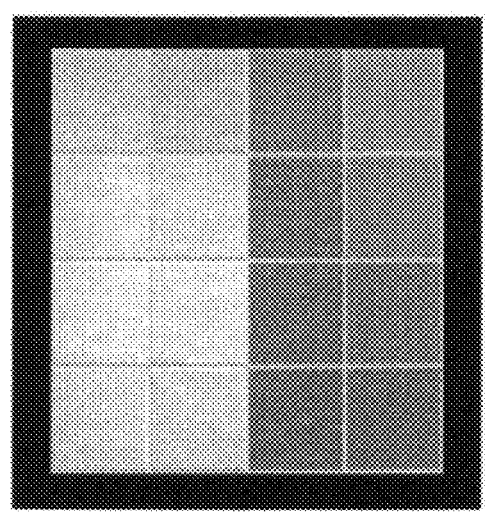

FIGS. 9A and 9B illustrate examples of images (computer-graphics (CG) images) of the planar object 10 displayed on the display unit 50. The planar object 10 is a printed material output based on electrophotography by varying the coverage using the cyan+silver toner, the magenta+silver toner, the magenta toner, and the cyan toner shown in FIG. 2. The images obtained are rendered by the rendering unit 48 based on the light source information (light source direction) acquired by the light source information acquiring unit 44 and the camera information (visual line direction) acquired by the camera information acquiring unit 46. A light source is disposed in the normal direction of the planar object 10 (at an incident angle of 0°). FIG. 9A illustrates a diffuse reflection image obtained when a camera is disposed at an angle of 45° relative to the normal direction of the planar object 10 and the planar object 10 is viewed at an angle. FIG. 9B illustrates a specular reflection image obtained when the camera is disposed in the normal direction of the planar object 10 and the planar object 10 is viewed from the front. A change of reflection color, particularly, a change of luster thereof, caused by a difference in viewing angle due to changing of the position of the camera is displayed. Specifically, a difference in a metallic luster region including silver toner and the reflectance thereof are clearly shown.

Figure 10A:
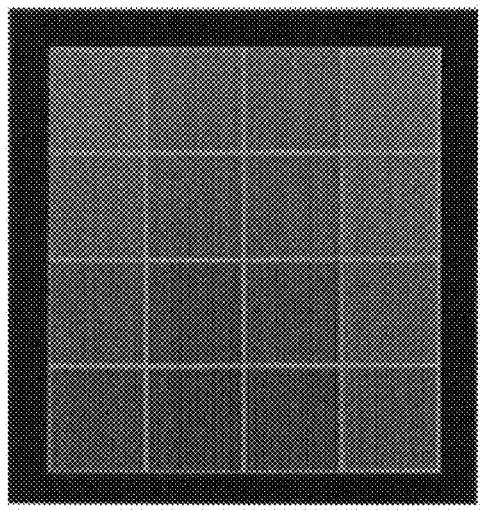
FIGS. 10A and 10B illustrate other images (CG images) displayed on the display unit according to the exemplary embodiment.
Figure 10B:
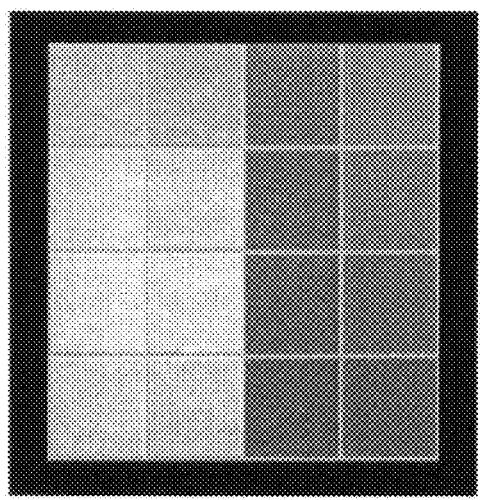

FIGS. 10A and 10B illustrate examples of images (CG images) of the planar object 10 displayed on the display unit 50. In these examples, a tablet terminal equipped with a tilt sensor is used as the display apparatus 25 shown in FIG. 4 and displays a change of luster of the planar object 10 caused as a result of changing the position of the light source in accordance with the tilt of the tablet terminal. The camera is disposed in the normal direction of the planar object 10. FIG. 10A illustrates a diffuse reflection image obtained when the tablet terminal is tilted such that light is received by the planar object 10 at an angle (at an incident angle of 45°). FIG. 10B illustrates a specular reflection image obtained when the tablet terminal is changed in angle such that light is received by the planar object 10 from the front (at an incident angle of 0°). By changing the position of the light source so that a change of luster of the planar object 10 caused by a difference in incident angle of light is dynamically displayed, the texture of the planar object 10 is reproduced realistically in three-dimensional computer graphics.

This exemplary embodiment is summarized as follows. Specifically, in order to display the reflection color of the planar object 10, the following two methods may be used.

The first method involves determining parameters of, for example, the Lambert reflection model and the Phong reflection model and performing display using the reflection models.

The second method involves acquiring diffuse reflection images and specular reflection images of multiple angles and performing display based on image interpolation.

Of these two methods, images under an enormous number of angle conditions are necessary in the second method, resulting in an increase in the amount of calculation. On the other hand, the first method may include a case where the diffuse reflectance and the specular reflectance are determined from the diffuse reflection image and the specular reflection image acquired by the texture scanner 5, as in this exemplary embodiment, and a case where the diffuse reflectance and the specular reflectance are determined from the diffuse reflection image and the specular reflection image acquired by the camera. In the case of the texture scanner 5, the specular reflectance for each pixel of a two-dimensional plane is calculated from a simple difference between the diffuse reflection image and the specular reflection image. However, in the case of the camera, such a simple difference may lead to uneven luster, thus making it difficult to properly extract luster information of the two-dimensional plane. Therefore, it is necessary to determine and estimate the specular reflectance from a large number of images by acquiring a large number of images with the camera. As a result, the amount of calculation is smaller with the texture scanner 5 than with the camera.

Second Exemplary Embodiment

In a second exemplary embodiment, the two difference images (specular reflection image-diffuse reflection image) and (diffuse reflection image-specular reflection image) are used as difference images between the diffuse reflection image and the specular reflection image.

Specifically, the reflectance distribution function calculating unit 42 uses the diffuse reflectance distribution function obtained by the diffuse reflectance distribution function calculating unit 36 and the specular reflectance distribution function obtained by the specular reflection distribution function calculating unit 38 so as to calculate reflection light intensity I(x, y) in a two-dimensional plane by using the following expression in accordance with the Lambert reflection model and the Phong reflection model:

$$I(x,y)=I_i \cdot \{w_d \cdot G_d(x,y) \cdot \cos\theta_i\}$$

$$+I_i \cdot \{w_{s1} \cdot \{G_s(x,y)-G_d(x,y)\} \cdot \cos^{n1}\gamma\} - I_i \cdot \{w_{s2} \cdot \{G_d(x,y)-G_s(x,y)\} \cdot \cos^{n2}\gamma\}$$

where $\{w_d \cdot G_d(x, y) \cdot \cos\theta_i\}$ denotes a diffuse reflectance distribution function, $w_d$ denotes a diffuse reflection weighting factor, $G_d$ denotes a diffuse reflection image, $\{w_{s1} \cdot \{G_s(x, y)-G_d(x, y)\} \cdot \cos^{n1}\gamma\}$ denotes a first specular reflection distribution function, $G_s(x, y)$ denotes a specular reflection image, $\{w_{s2} \cdot \{G_d(x, y)-G_s(x, y)\} \cdot \cos^{n2}\gamma\}$ denotes a second specular reflection distribution function, $w_{s1}$ and $w_{s2}$ denote specular reflection weighting factors, and $n_1$ and $n_2$ denote specular reflection indices. The difference images are difference images (specular reflection image-diffuse reflection image) and (diffuse reflection image-specular reflection image), and a pixel with a negative difference value is set as 0.

The diffuse reflectance distribution function calculating unit 36 calculates diffuse reflectance from the diffuse reflection image and the diffuse reflection weighting factor, and the specular reflection distribution function calculating unit 38 calculates specular reflectance from the two difference images and the two specular reflection weighting factors.

In this reflection model, the parameters including the diffuse reflection weighting factor $w_d$, the specular reflection weighting factors $w_{s1}$ and $w_{s2}$, and the specular reflection indices $n_1$ and $n_2$ are set in advance to fixed values by the parameter adjusting unit 40 in accordance with the reflection characteristics of the target object and the output characteristics of the display apparatus 25.

Figure 11A:
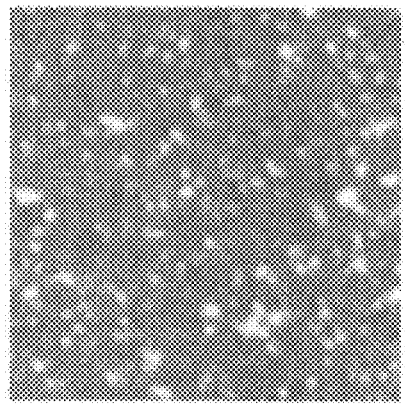
FIGS. 11A to 11D illustrate a diffuse reflection image, a specular reflection image, and two difference images according to an exemplary embodiment.
Figure 11B:
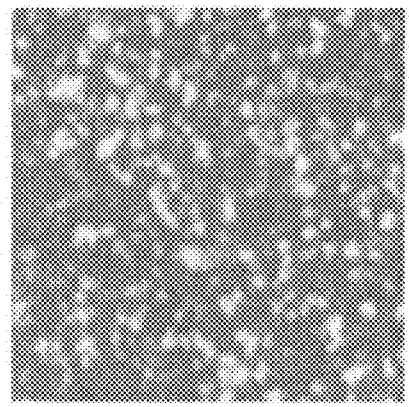
Figure 11C:
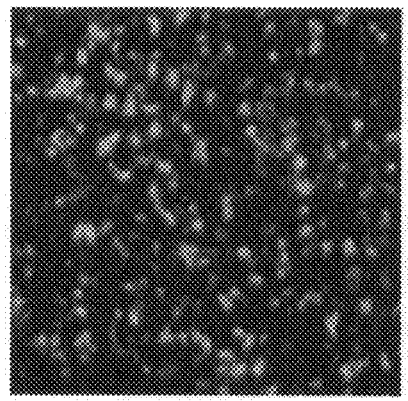
Figure 11D:
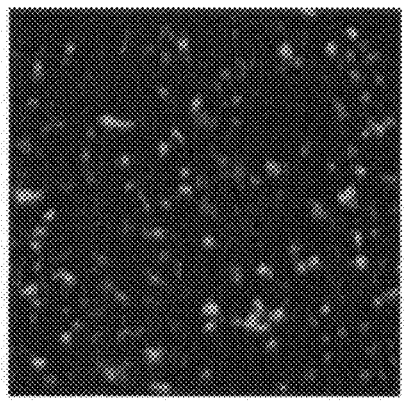

FIGS. 11A to 11D illustrate examples of a diffuse reflection image, a specular reflection image, and difference images of the planar object 10 obtained by the texture scanner 5 shown in FIG. 1 in accordance with this exemplary embodiment. The planar object 10 is composed of a pearl-pigment-containing material, and in these images, reflection light from each pixel spreads not only in the specular reflection direction but also in various angular directions. FIG. 11A illustrates a diffuse reflection image, FIG. 11B illustrates a specular reflection image, and FIGS. 11C and 11D illustrate difference images. Specifically, FIG. 11C illustrates a difference image (specular reflection image-diffuse reflection image), and FIG. 11D illustrates a difference image (diffuse reflection image-specular reflection image). Unlike the first exemplary embodiment, since the difference image (specular reflection image-diffuse reflection image) has an increased number of pixels having negative difference values, the specular reflectance distribution function is calculated by adding the difference image (diffuse reflection image-specular reflection image) in which the difference value of the difference image (specular reflection image-diffuse reflection image) is a negative value. The diffuse reflectance distribution function is calculated from the image in FIG. 11A, and the specular reflectance distribution function is calculated from the images in FIGS. 11C and 11D.

Figure 12A:
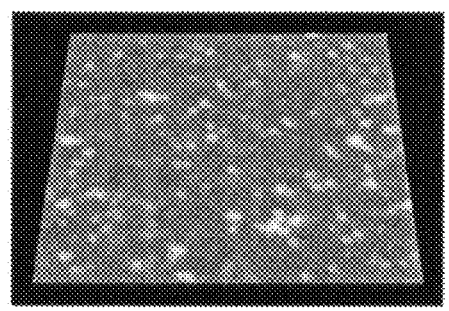
FIGS. 12A to 12C illustrate images (CG images) displayed on the display unit according to the exemplary embodiment.
Figure 12B:
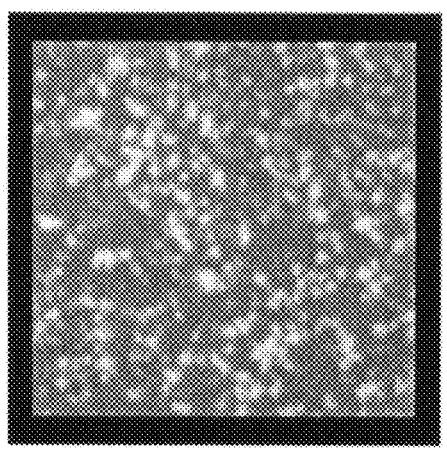
Figure 12C:
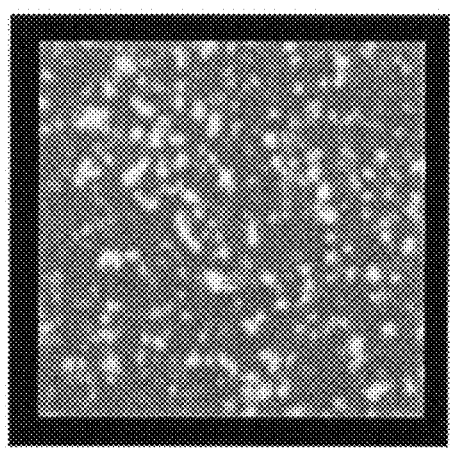

FIGS. 12A to 12C illustrate examples of images (CG images) of the planar object 10 in FIGS. 11A to 11D. A light source is disposed in the normal direction of the planar object 10 (at an incident angle of 0°). FIG. 12A illustrates a diffuse reflection image obtained when a camera is disposed at an angle of 45° relative to the normal direction of the planar object 10 and the planar object 10 is viewed at an angle. FIGS. 12B and 12C illustrate specular reflection images obtained when the camera is disposed in the normal direction of the planar object 10 and the planar object 10 is viewed from the front. Specifically, the image shown in FIG. 12B corresponds to the specular reflectance distribution function calculated based on the difference image (specular reflection image-diffuse reflection image) in accordance with the first exemplary embodiment for a comparison, and the image shown in FIG. 12C corresponds to the specular reflectance distribution function calculated based on the two difference images (specular reflection image-diffuse reflection image) and (diffuse reflection image-specular reflection image) in accordance with the second exemplary embodiment.

In the image according to the first exemplary embodiment shown in FIG. 12B, pixels that are brighter than those in the actual specular reflection image increase in number, whereas, in the image according to the second exemplary embodiment shown in FIG. 12C, the luster reproduced is similar to that of an actual object since pixels with a negative difference value of the difference image (specular reflection image-diffuse reflection image) are taken into consideration.

Accordingly, with respect to a material in which the specular reflectance distribution varies from micro region to micro region, the texture of the object surface may still be displayed in accordance with a simple calculation using a small amount of image data.

Third Exemplary Embodiment

In the first and second exemplary embodiments, the texture scanner 5 is used to acquire a diffuse reflection image and a specular reflection image of a planar object so as to computer-graphically reproduce the texture of the planar object. In a third exemplary embodiment, the texture scanner 5 may be used to acquire a diffuse reflection image and a specular reflection image of a planar object so as to computer-graphically reproduce the texture of a three-dimensional object.

Specifically, as shown in FIG. 13, a shape information acquiring unit 45 is added so as to acquire a three-dimensional shape model that reproduces the texture. Based on light source information (light source direction) acquired by the light source information acquiring unit 44, camera information (visual line direction) acquired by the camera information acquiring unit 46, and shape information acquired by the shape information acquiring unit 45, a three-dimensional model is rendered on a virtual screen set within a virtual three-dimensional space so that the texture of a three-dimensional object is computer-graphically reproduced, and the three-dimensional model is then displayed on the display unit 50. Consequently, a change of reflection color caused when the texture of a planar object is transferred to a freely-chosen three-dimensional shape model may be displayed.

Although exemplary embodiments of the present invention have been described above, the exemplary embodiments of the present invention are not limited to these exemplary embodiments, and various modifications are permissible.

For example, although the specular reflection index n used has the same value among the pixels in the two-dimensional plane, the specular reflection index n may be varied from pixel to pixel in accordance with the following expression:

$$I(x,y)=I_i \cdot \{w_d \cdot G_d(x,y) \cdot \cos \theta_i\} + I_i \cdot \{w_s \cdot \{G_s(x,y) - G_d(x,y)\} \cdot \cos^{n(x,y)} \gamma\}$$

For example, the specular reflection index n may be set as a function of the difference image between the diffuse reflection image and the specular reflection image in accordance with the following expression, such that n increases with increasing luminance of the difference image:

$$n(x,y)=f(G_s(x,y)-G_d(x,y))$$

Furthermore, although the Phong reflection model is used in the above exemplary embodiments, the Torrance-Sparrow reflection model or the Cook-Torrance reflection model may be used as an alternative.

Figure 14:
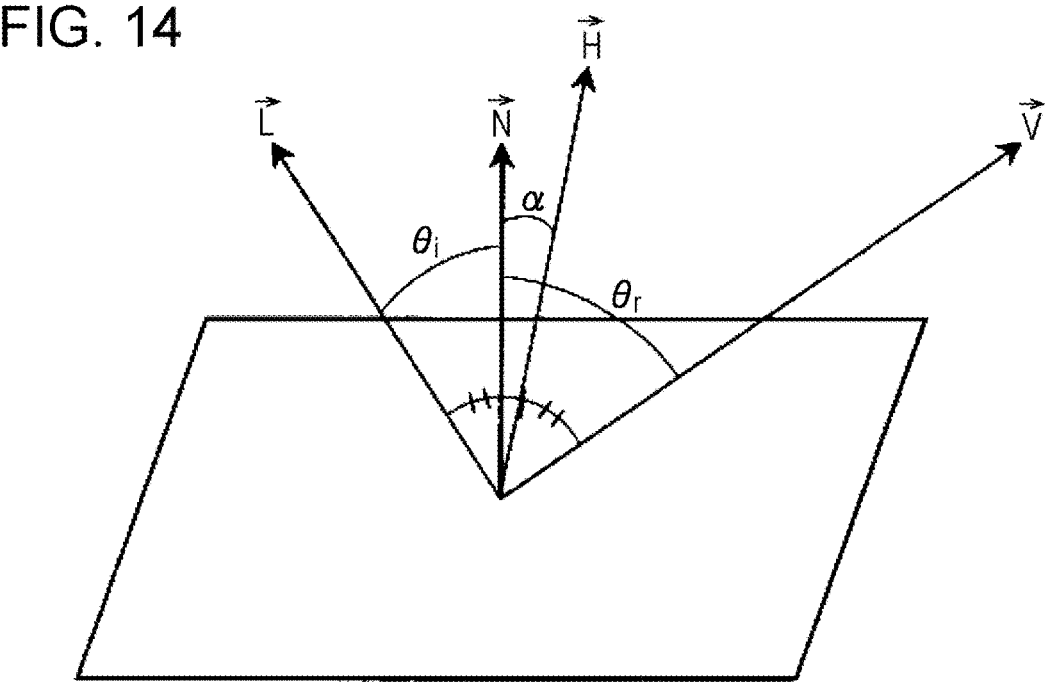
FIG. 14 illustrates the Torrance-Sparrow reflection model.

FIG. 14 illustrates the Torrance-Sparrow reflection model. Assuming that $I_i$ denotes incident light intensity, $w_s$ denotes a specular reflection weighting factor, $G_s(x, y)$ denotes a specular reflection image, $G_d(x, y)$ denotes a diffuse reflection image, α denotes an angle at which a bisector of an incident angle and a reflection angle forms a normal line, σ denotes surface roughness, and $\theta_r$ denotes a reflection angle, specular reflection light intensity $I_s(x, y)$ in a two-dimensional plane is expressed as follows:

$$I_s(x, y) = I_i \cdot w_s \cdot \{G_s(x, y) - G_d(x, y)\} \cdot \frac{\exp(-\alpha^2/2\sigma^2)}{\cos\theta_r}$$

In this reflection model, the parameters including the specular reflection weighting factor $w_s$ and the surface roughness σ are set in advance to fixed values by the parameter adjusting unit 40 in accordance with the reflection characteristics of the target object and the output characteristics of the display apparatus 25.

With regard to the Cook-Torrance reflection model, assuming that $I_i$ denotes incident light intensity, $w_s$ denotes a specular reflection weighting factor, $G_s(x, y)$ denotes a specular reflection image, $G_d(x, y)$ denotes a diffuse reflection image, α denotes an angle at which a bisector of an incident angle and a reflection angle forms a normal line, m denotes surface roughness, and $\theta_r$ denotes a reflection angle, specular reflection light intensity $I_s(x, y)$ in a two-dimensional plane is expressed as follows:

$$I_s(x, y) = I_i \cdot w_s \cdot \{G_s(x, y) - G_d(x, y)\} \cdot \frac{\exp(-\tan^2\alpha/m^2)}{m^2\cos^4\alpha \cdot \cos\theta_r}$$

In this reflection model, the parameters including the specular reflection weighting factor $w_s$ and the surface roughness m are set in advance to fixed values by the parameter adjusting unit 40 in accordance with the reflection characteristics of the target object and the output characteristics of the display apparatus 25.

Furthermore, although the parameters including the diffuse reflection weighting factor $w_d$, the specular reflection weighting factor $w_s$, and the specular reflection index n are set in advance to fixed values by the parameter adjusting unit 40, a parameter adjustment function may be displayed on the display unit 50, such that the reflection color of the CG image may be varied by changing the parameters on the display unit 50.

For example, the weighting factors may be varied, and the reflectance distribution function may be evaluated by using a fixed evaluation function, such that a reflectance distribution function with a relatively high evaluation value may be selected. Then, CG images with varied weighting factors may be sequentially displayed on the display unit 50, and the user may select a weight considered to be optimal.

Although a difference image is calculated by the difference image acquiring unit 34 of the display apparatus 25 in each of the above exemplary embodiments, as shown in FIG. 4, the texture scanner 5 shown in FIG. 1 may be equipped with an arithmetic unit that calculates a difference between a diffuse reflection image and a specular reflection image and outputs the difference to an external apparatus.

Figure 15:
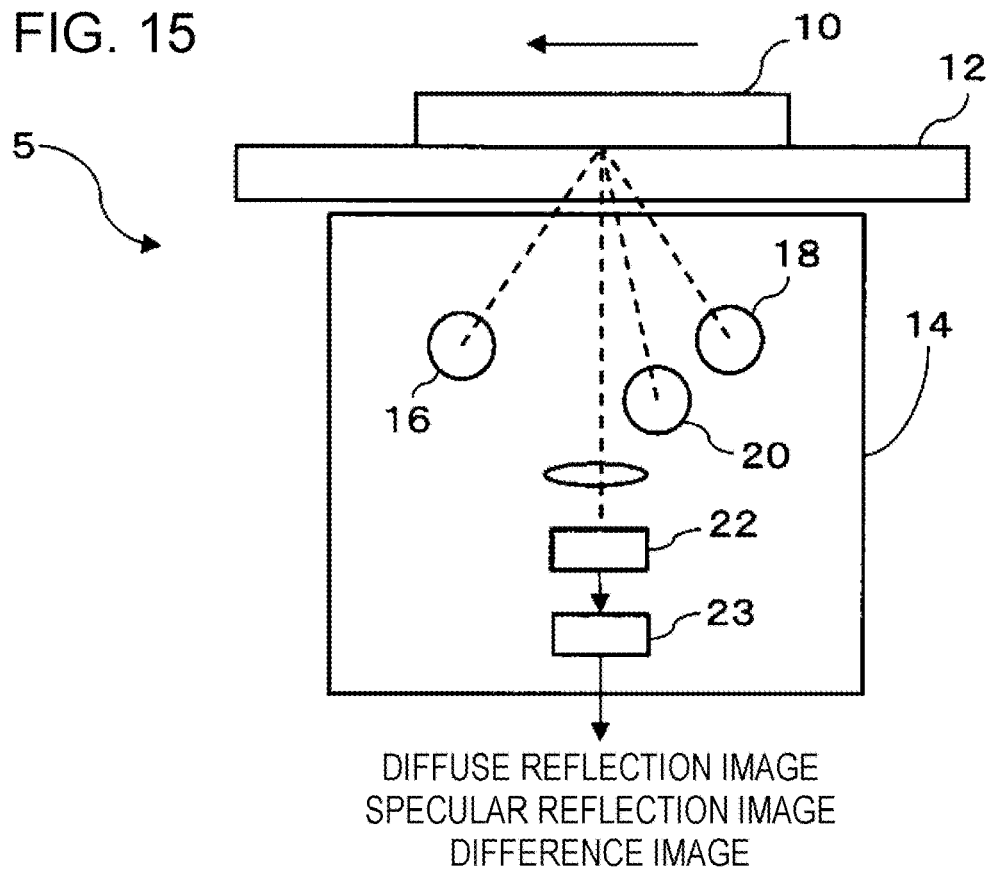
FIG. 15 illustrates the configuration of a texture scanner according to a modification.

FIG. 15 illustrates another configuration of the texture scanner 5. In addition to the components of the texture scanner 5 shown in FIG. 1, the texture scanner 5 includes an arithmetic unit 23. The arithmetic unit 23 generates a difference image by calculating a difference between a diffuse reflection image and a specular reflection image, and outputs the difference image to an external apparatus. Therefore, the texture scanner 5 outputs a diffuse reflection image, a specular reflection image, and a difference image from an output interface to the external apparatus. The difference image is at least one of a difference image (diffuse reflection image-specular reflection image) and a difference image (specular reflection image-diffuse reflection image). The external apparatus may be the display apparatus 25 or an external server, or may be a portable memory, such as a universal-serial-bus (USB) memory or a secure-digital (SD) card.

Furthermore, a CG image created and displayed by the display apparatus 25 shown in FIG. 4 may be appropriately registered in the server via a network, so as to form a CG-image database.

Figure 16:
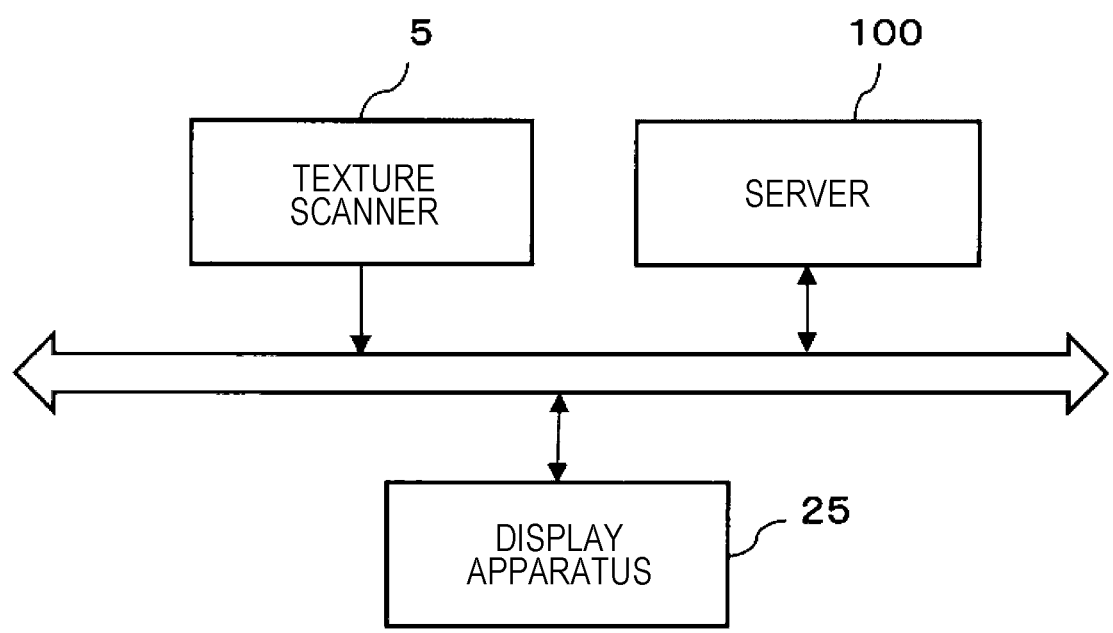
FIG. 16 illustrates a system configuration according to a modification.

FIG. 16 illustrates a system configuration according to a modification. The texture scanner 5, a server 100, and the display apparatus 25 are connected to one another in a data exchangeable fashion via a network. A diffuse reflection image, a specular reflection image, and a difference image obtained by the texture scanner 5 are transmitted to the server 100 via the network and are stored in the server 100. The display apparatus 25 accesses the server 100 to acquire the diffuse reflection image, the specular reflection image, and the difference image, calculates a reflectance distribution function, and causes the display unit 50 to display the reflection color. A CG image displayed by the display apparatus 25 is transmitted to the server 100 via a communication interface and the network and is stored in the server 100, and is also transmitted to another apparatus when requested from the display apparatus. The server 100 may display a list of CG images uploaded from the display apparatus 25 in another display apparatus in the form of thumbnail images, and may allow for selection of the CG images in the other display apparatus.

The foregoing description of the exemplary embodiments of the present invention has been provided for the purposes of illustration and description. It is not intended to be exhaustive or to limit the invention to the precise forms disclosed. Obviously, many modifications and variations will be apparent to practitioners skilled in the art. The embodiments were chosen and described in order to best explain the principles of the invention and its practical applications, thereby enabling others skilled in the art to understand the invention for various embodiments and with the various modifications as are suited to the particular use contemplated. It is intended that the scope of the invention be defined by the following claims and their equivalents.

What is claimed is:

1. A display apparatus comprising:
   a processor configured to
      acquire an image signal of an object surface, wherein the image signal comprising a diffuse reflection image of the object surface and a specular reflection image of the object surface,
      acquire a difference image between the diffuse reflection image and the specular reflection image, wherein the difference image acquired by the processor includes an image obtained by subtracting the diffuse reflection image from the specular reflection image and an image obtained by subtracting the specular reflection image from the diffuse reflection image, and
      calculate a reflectance distribution function of the object surface by using a diffuse reflectance distribution function calculated from the diffuse reflection image, a first specular reflectance distribution function calculated from the image obtained by subtracting the diffuse reflection image from the specular reflection image, and a second specular reflectance distribution function calculated from the image obtained by subtracting the specular reflection image from the diffuse reflection image; and
   a display that displays a reflection color of the object surface in accordance with a change of orientation of the object surface by using the reflectance distribution function.

2. The display apparatus according to claim 1,
   wherein the reflectance distribution function is calculated from the diffuse reflectance distribution function, a function obtained by multiplying the first specular reflectance distribution function by a weight w1, and a function obtained by multiplying the second specular reflectance distribution function by a weight w2, and
   wherein the reflectance distribution function is calculated while varying the weight w1 and the weight w2.

3. The display apparatus according to claim 1,
   wherein the diffuse reflection image and the specular reflection image are images obtained by scanning the object surface by using a scanner including a first light source and a second light source, the first light source radiating light onto the object surface at a first incident angle, the second light source radiating light onto the object surface at a second incident angle different from the first incident angle.

4. The display apparatus according to claim 3,
wherein the first incident angle is 45°, and the second incident angle ranges between 5° and 10°.

5. A scanner comprising:
a first light source that radiates light onto an object surface at a first incident angle;
a second light that radiates light onto the object surface at a second incident angle different from the first incident angle;
a processor configured to
   acquire an image signal of the object surface, wherein the image signal comprising a diffuse reflection image of the object surface and a specular reflection image of the object surface,
   calculate a difference image between the diffuse reflection image of the object surface and the specular reflection image of the object surface, the diffuse reflection image being obtained as a result of the object surface being irradiated with the light at the first incident angle, the specular reflection image being obtained as a result of the object surface being irradiated with the light at the second incident angle,
wherein the first incident angle is 45° to the object surface, and the second incident angle ranges between 5° and 10° to the object surface; and
an output that outputs the diffuse reflection image, the specular reflection image, and the difference image.

6. A non-transitory computer readable medium storing a program causing a computer to execute a process, the process comprising:
acquire an image signal of an object surface, wherein the image signal comprising a diffuse reflection image of the object surface and a specular reflection image of the object surface;
storing the diffuse reflection image and the specular reflection image in a memory;
acquiring a difference image between the diffuse reflection image and the specular reflection image, wherein the difference image includes an image obtained by subtracting the diffuse reflection image from the specular reflection image and an image obtained by subtracting the specular reflection image from the diffuse reflection image, and storing the difference image in the memory;
calculating a reflectance distribution function of the object surface by using a diffuse reflectance distribution function calculated from the diffuse reflection image, a first specular reflectance distribution function calculated from the image obtained by subtracting the diffuse reflection image from the specular reflection image, and a second specular reflectance distribution function calculated from the image obtained by subtracting the specular reflection image from the diffuse reflection image; and
causing a display to display a reflection color of the object surface in accordance with a change of orientation of the object surface by using the reflectance distribution function.

\* \* \* \* \*